US00PP23102P2

(12) United States Plant Patent
Bergman

(10) Patent No.: US PP23,102 P2
(45) Date of Patent: Oct. 9, 2012

(54) ***CHRYSANTHEMUM* PLANT NAMED 'CIDZ0010'**

(50) Latin Name: *Chrysanthemum×morifolium*
Varietal Denomination: CIDZ0010

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,575

(22) Filed: Aug. 4, 2011

(51) Int. Cl.
*A01H 5/00* (2006.01)

(52) U.S. Cl. ..... Plt./287

(58) Field of Classification Search ..... Plt./287
See application file for complete search history.

*Primary Examiner* — Kent L Bell
(74) *Attorney, Agent, or Firm* — Joshua L. Price

(57) ABSTRACT

A new *Chrysanthemum* plant named 'CIDZ0010' particularly distinguished by the spoon-type yellow and orange-red bicolored ray florets, dark yellow-green foliage, excellent flowering uniformity, good branching and an eight week flowering response.

1 Drawing Sheet

Latin name of the genus and species of the plant claimed: *Chrysanthemum×morifolium.*

Varietal denomination: 'CIDZ0010'.

BACKGROUND OF THE NEW PLANT

The present invention comprises a new *Chrysanthemum*, botanically known as *Chrysanthemum×morifolium*, and hereinafter referred to by the variety name 'CIDZ0010'.

'CIDZ0010' is a product of a planned breeding program. The new cultivar has spoon-type yellow and orange-red bicolored ray florets, dark yellow-green foliage, excellent flowering uniformity, good branching and an eight week flowering response.

'CIDZ0010' originated from a hybridization made in June 2006 in a controlled breeding environment in Salinas, Calif., USA. The female parent was the proprietary plant designated 'YB-B0607', unpatented, with bronze ray floret color and fewer disc florets.

The male parent of 'CIDZ0010' was an unpatented, proprietary plant identified as 'YB-A8052' with dark yellow, spoon-type ray florets. The resultant seed was sown in October 2006 in Fort Myers, Fla., USA.

'CIDZ0010' was selected as one flowering plant within the progeny of the stated cross in March 2007 in a controlled environment in Fort Myers, Fla., USA.

The first act of asexual reproduction of 'CIDZ0010' was accomplished when vegetative cuttings were propagated from the initial selection in June 2007 in a controlled environment in Fort Myers, Fla., USA.

BRIEF SUMMARY OF INVENTION

Horticultural examination of plants grown from cuttings of the plant initiated in June 2007, and continuing thereafter, has demonstrated that the combination of characteristics as herein disclosed for 'CIDZ0010' are firmly fixed and are retained through successive generations of asexual reproduction.

'CIDZ0010' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7068). 'CIDZ0010' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIDZ0010' with colors being as true as possible with an illustration of this type.

Figure 1:
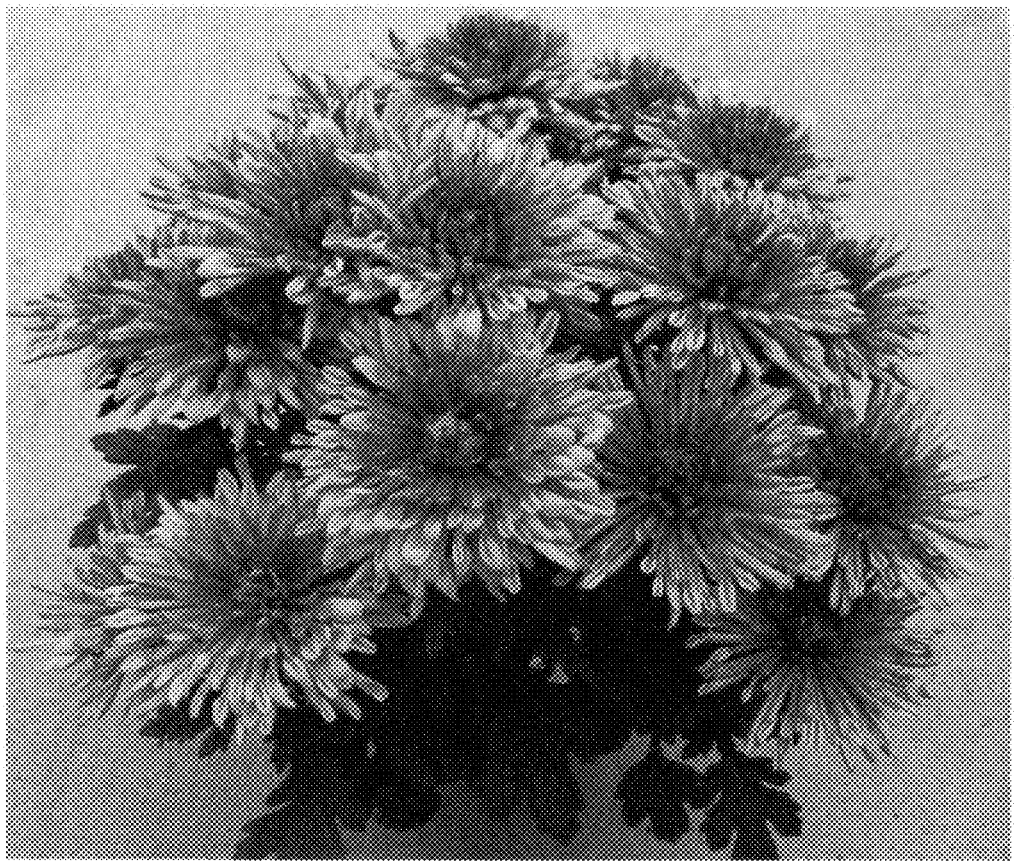
Figure 2:
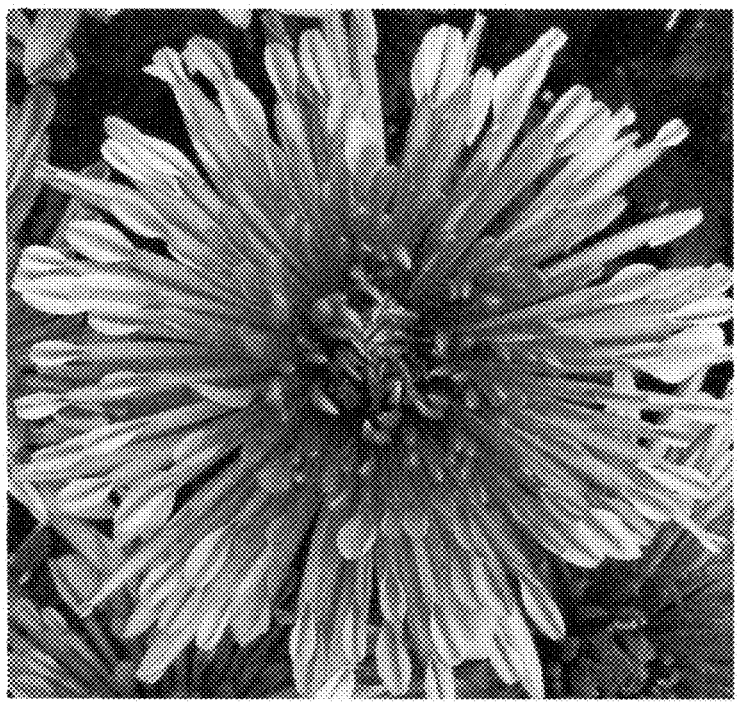

The photographic drawing shows in FIG. 1 four flowering potted plants of the new variety, and in FIG. 2 a close-up of the inflorescence.

DETAILED BOTANICAL DESCRIPTION

The plant descriptions, measurements and aforementioned photographs were taken in Gilroy, Calif. in early May 2011 under natural light. These plants were propagated and grown in Nipomo, Calif. and shipped to Gilroy, Calif. for the data collection and photographs. These plants were approximately eleven weeks of age; grown as four plants together in a six inch pot under greenhouse trial conditions.

Color references are made to The Royal Horticultural Society Colour Chart (R.H.S.) 2001.

TABLE 1

DIFFERENCES BETWEEN THE NEW VARIETY 'CIDZ0010' AND A SIMILAR VARIETY

| | 'CIDZ0010' | 'Dazzling Yonew York' (U.S. Plant Pat. No. 17,438) |
|---|---|---|
| Inflorescence diameter: | Larger | Smaller |
| Quantity of ray florets: | Little less | Little more |
| Ray florets: | Spoon-type | Flat |
| Quantity of disc florets: | Many more | Much fewer |

Plant:

*Form, growth and habit.*—Herbaceous decorative pot-type, stems upright, freely branching, strong and moderately vigorous growth habit.

*Plant height.*—18.0 cm.

*Plant height (inflorescence included).*—24-26.0 cm.

*Plant width.*—20-24.0 cm.

Roots:

*Number of days to initiate roots.*—About 4 days at about 22 degrees C.

*Number of days to produce a rooted cutting.*—About 10 days at 22 degrees C.

*Type.*—Fine, fibrous, free branching.

*Color.*—RHS N155B but whiter.

Foliage:

*Arrangement.*—Alternate, simple.

*Immature, leaf color, upper surface.*—Closest to RHS 147A.

*Lower surface.*—RHS 137B but appears lighter due to hairs.

*Mature, leaf color, upper surface.*—Closest to RHS 147A.

*Lower surface.*—RHS 137B but appears lighter due to hairs.

*Length.*—6.5-7.5 cm.

*Width.*—4.9-5.7 cm.

*Shape.*—Ovate.

*Base shape.*—Attenuate.

*Apex shape.*—Mucronulate.

*Margin.*—Palmately lobed; irregularly serrate.

*Texture, upper surface.*—Bifid T-shaped hairs.

*Lower surface.*—Bifid T-shaped hairs.

*Color of veins, upper surface.*—RHS 147B but lighter.

*Color of veins, lower surface.*—RHS 147B but lighter.

*Petiole color.*—RHS 147B but lighter.

*Length.*—2.3-2.5 cm.

*Diameter.*—0.2-0.3 cm.

*Texture.*—Bifid T-shaped hairs.

Stem:

*Quantity of main branches per plant.*—4-5.

*Color of stem.*—RHS 137B but appears lighter due to hairs.

*Length of stem.*—20.-21.0 cm.

*Diameter.*—0.4-0.45 cm.

*Length of internodes.*—1.5-2.5 cm.

*Texture.*—Bifid T-shaped hairs.

*Color of peduncle.*—RHS 137B but appears lighter due to hairs.

*Length of peduncle.*—2.0-2.5 cm.

*Peduncle diameter.*—0.4 cm.

*Texture.*—Bifid T-shaped hairs.

Inflorescence:

*Type.*—Compositae type, solitary inflorescences, decorative-type, borne terminally above foliage, ray florets arranged acropetally on a capitulum.

*Quantity of short days to flowering (response time).*—About 8 weeks.

*Quantity of inflorescences per plant.*—4-5.

*Lastingness of individual blooms on the plant.*—About 4 weeks.

*Fragrance.*—Slightly spicy.

Bud (just when opening/showing color):

*Color.*—RHS 10D ground with RHS 35D upper with darker, irregular streaks of RHS 35C.

*Length.*—1.0-1.5 cm.

*Width.*—1.5 cm.

*Shape.*—Oblate.

Immature inflorescence:

*Diameter.*—8-10.0 cm.

*Color of ray florets, upper surface.*—Closest to RHS N34A quickly having slight striations and apices of RHS 5A.

*Lower surface.*—Closest to RHS N34A quickly having slight striations and apices of RHS 5A.

Mature inflorescence:

*Diameter.*—11-13 cm.

*Depth.*—2.5-3.0 cm.

*Total diameter of 'disc'.*—2.0-2.3 cm.

*Receptacle height.*—0.7-0.8 cm.

*Receptacle diameter.*—1.2 cm.

Ray florets:

*Average quantity of florets.*—Approximately 100 in numerous whorls.

*Color of florets, upper surface.*—RHS 12B ground color overlaid with slight striations of RHS 34B to RHS 34C, maturing to more yellow looking as it loses the red, becoming RHS 9C with slight striations of RHS 34C to RHS 34D and finally fading to more RHS 8B with hardly any red color.

*Lower surface.*—RHS 12C overlaid with irregular shades of RHS N34C.

*Length.*—4.6-5.5 cm.

*Width.*—0.6-1.1 cm.

*Shape.*—Initially spoon and most mature to totally open elliptical.

*Apex shape.*—Mostly obtuse.

*Margin.*—Entire; slightly fused.

*Texture, upper surface.*—Papillose.

*Lower surface.*—Papillose.

Disc florets:

*Average quantity of florets.*—Approximately 120.

*Color of florets.*—RHS 1C but greener and with RHS 6A apex.

*Length.*—0.8 cm.

*Width.*—0.1 cm.

*Shape.*—Tubular, elongated.

*Apex shape.*—Acute, 5 pointed.

Phyllaries:

*Quantity.*—Approximately 70.

*Color, upper surface.*—Closest to RHS 137A.

*Lower surface.*—RHS C137A but appears lighter due to hairs.

*Length.*—0.4-0.5 cm.

*Width.*—0.1-0.2 cm.

*Shape.*—Lanceolate.

*Apex shape.*—Acute.

*Base*.—Fused.
*Margins*.—Entire; inner ones are more papery or translucent.
*Texture, upper surface*.—Glabrous.
*Lower surface*.—Bifid T-shaped hairs.

Reproductive organs:
*Pistil*.—1.
*Found on both florets*.—Yes.
*Length*.—0.7-0.8 cm.
*Style color*.—RHS 1C but more green.
*Style length*.—0.8 cm.
*Stigma color*.—RHS 6A.
*Stigma shape*.—Bi-parted.
*Ovary color*.—Not observed.
*Stamens*.—4.
*Found on only disc florets*.—Yes.
*Color of filaments*.—RHS 155C.
*Length filaments*.—0.3-0.4 cm.
*Anther color*.—RHS 13A.
*Anther length*.—0.1 cm.
*Anther shape*.—Oblong.
*Color of pollen*.—Not observed.
*Pollen amount*.—Not observed.
*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'CIDZ0010' substantially as illustrated and described herein.

* * * * *